(12) United States Patent
Nishiwaki et al.

(10) Patent No.: US 10,596,344 B2
(45) Date of Patent: Mar. 24, 2020

(54) ANESTHESIA DEVICE AND METHOD OF CONTROLLING HYDROGEN CONCENTRATION IN A HYDROGEN-CONTAINING ANESTHESIA GAS

(71) Applicant: TAIYO NIPPON SANSO CORPORATION, Tokyo (JP)

(72) Inventors: Yoshiki Nishiwaki, Funabashi (JP); Tomiei Kazama, Tokorozawa (JP); Yasushi Satoh, Tokorozawa (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 307 days.

(21) Appl. No.: 15/544,348

(22) PCT Filed: Jan. 19, 2016

(86) PCT No.: PCT/JP2016/051399
§ 371 (c)(1),
(2) Date: Jul. 18, 2017

(87) PCT Pub. No.: WO2016/117538
PCT Pub. Date: Jul. 28, 2016

(65) Prior Publication Data
US 2017/0368293 A1    Dec. 28, 2017

(30) Foreign Application Priority Data
Jan. 21, 2015 (JP) .................................. 2015-009352

(51) Int. Cl.
*A61M 16/10* (2006.01)
*A61D 7/04* (2006.01)
(Continued)

(52) U.S. Cl.
CPC ............. *A61M 16/104* (2013.01); *A61D 7/04* (2013.01); *A61K 31/02* (2013.01); *A61K 31/08* (2013.01);
(Continued)

(58) Field of Classification Search
CPC ............ A61M 16/104; A61M 16/0891; A61M 16/0093; A61M 16/024; A61M 16/122;
(Continued)

(56) References Cited

U.S. PATENT DOCUMENTS 3,814,092 A * 6/1974 Simionescu .......... A61M 16/08
                                                     128/203.28
4,015,599 A * 4/1977 Peterson ................ A61K 9/007
                                                     128/204.13
(Continued)

FOREIGN PATENT DOCUMENTS

| JP | 44-018160 | 8/1969 |
| JP | 55-129134 | 10/1980 |

(Continued)

OTHER PUBLICATIONS

International Search Report for PCT/JP2016/051399 dated Apr. 5, 2016, 3 pages.

*Primary Examiner* — Kendra D Carter
*Assistant Examiner* — Thao Tran
(74) *Attorney, Agent, or Firm* — Nixon & Vanderhye P.C.

(57) ABSTRACT

An anesthesia device configured to measure the hydrogen concentration in an anesthesia gas containing a hydrogen gas includes: an anesthesia gas preparation circuit configured to generate anesthesia gas by mixing an air or an oxygen mixture air with a vaporized anesthetic; a closed circuit-type or semi-closed circuit-type respiratory circuit including a gas circulation passage configured to circulate the hydrogen-containing anesthesia gas containing the hydrogen gas and
(Continued)

the vaporized anesthetic; and a hydrogen concentration measurement circuit configured to measure the hydrogen concentration in the hydrogen-containing anesthesia gas in the gas circulation passage, wherein the hydrogen concentration measurement circuit includes: an anesthetic removing member having a removability of the vaporized anesthetic in the hydrogen-containing anesthesia gas; and a hydrogen concentration measuring instrument provided on the secondary side of the anesthetic removing member.

8 Claims, 2 Drawing Sheets

(51) Int. Cl.
| | | |
|---|---|---|
| *A61M 16/01* | (2006.01) | |
| *A61M 16/00* | (2006.01) | |
| *A61M 16/08* | (2006.01) | |
| *A61M 16/12* | (2006.01) | |
| *A61M 16/22* | (2006.01) | |
| *A61M 16/18* | (2006.01) | |
| *A61K 31/02* | (2006.01) | |
| *A61K 31/08* | (2006.01) | |

(52) U.S. Cl.
CPC ........ *A61M 16/0093* (2014.02); *A61M 16/01* (2013.01); *A61M 16/024* (2017.08); *A61M 16/0891* (2014.02); *A61M 16/122* (2014.02); *A61M 16/009* (2013.01); *A61M 16/18* (2013.01); *A61M 16/22* (2013.01); *A61M 2016/0039* (2013.01); *A61M 2016/1035* (2013.01); *A61M 2202/0241* (2013.01)

(58) Field of Classification Search
CPC .... A61M 16/01; A61M 16/009; A61M 16/22; A61M 2202/0241; A61M 2016/0039; A61M 16/0003; A61M 2016/1035; A61M 16/18; A61M 16/10; A61M 16/12; A61M 2016/102; A61M 11/00; A61M 11/06; A61M 13/00; A61M 13/003; A61M 15/0015; A61M 15/0018; A61M 15/0086; A61M 15/0088; A61M 15/009; A61M 16/0045; A61M 16/0051; A61M 16/0078; A61M 16/0096; A61M 16/04; A61M 16/042; A61M 16/06; A61M 16/0627; A61M 16/0677; A61M 16/08; A61M 16/0808; A61M 16/0816; A61M 16/0833; A61M 16/085; A61M 16/0858; A61M 16/1005; A61M 16/101; A61M 16/1015; A61M 16/1065; A61M 16/1095; A61M 16/14; A61M 16/16; A61M 16/161; A61M 16/202; A61M 16/203; A61M 16/204; A61M 16/205; A61M 2016/0021; A61M 2016/0024; A61M 2016/0027; A61M 2016/003; A61M 2016/0036; A61M 2016/0042; A61M 2016/1025; A61M 2016/103; A61M 2202/0007; A61M 2202/0208; A61M 2202/0225; A61M 2202/0233; A61M 2202/025; A61M 2202/0258; A61M 2202/0266; A61M 2202/0275; A61M 2202/0283; A61M 2202/0291; A61M 2205/15; A61M 2205/17; A61M 2205/18; A61M 2205/3331; A61M 2205/3334; A61M 2205/3344; A61M 2205/3355; A61M 2205/3368; A61M 2205/36; A61M 2205/50; A61M 2205/502; A61M 2205/505; A61M 2205/702; A61M 2205/75; A61M 2206/14; A61M 2230/43; A61M 2230/432; A61M 2230/435; A61M 2230/437; A61M 2230/50; A61D 7/04; A61K 31/02; A61B 5/082; A61B 5/091; G01N 1/22; G01N 1/2202; G01N 1/2205; A62B 7/14; B63C 11/22; Y10T 137/2499; Y10T 137/87652

See application file for complete search history.

(56) References Cited

U.S. PATENT DOCUMENTS

| | | | |
|---|---|---|---|
| 4,259,303 A | | 3/1981 | Nakaji et al. |
| 5,928,411 A | * | 7/1999 | Falb .................... A61M 16/009 95/129 |
| 6,076,392 A | * | 6/2000 | Drzewiecki ....... A61M 16/0051 73/23.2 |
| 6,131,571 A | * | 10/2000 | Lampotang ........... A61M 16/00 128/204.18 |
| 6,523,537 B1 | * | 2/2003 | Mas Marfany ....... A61M 16/18 128/203.12 |
| 7,219,666 B2 | * | 5/2007 | Friberg ............... A61M 16/024 128/203.12 |
| 8,393,321 B2 | * | 3/2013 | Burns, Jr. ............. A61K 31/06 128/203.11 |
| 2003/0176804 A1 | * | 9/2003 | Melker .................... A61B 5/08 600/532 |
| 2004/0107831 A1 | | 6/2004 | Graham et al. |
| 2005/0076911 A1 | * | 4/2005 | Fuhrman ............... A61M 16/01 128/205.12 |
| 2009/0301401 A1 | | 12/2009 | Kawano |
| 2015/0047634 A1 | * | 2/2015 | Murphy ........... A61M 16/0078 128/202.26 |
| 2015/0059743 A1 | * | 3/2015 | Aikawa ................. A61M 16/12 128/203.12 |
| 2015/0079197 A1 | * | 3/2015 | Kazama ................ A61K 31/05 424/600 |
| 2015/0258298 A1 | | 9/2015 | Satoh et al. |

FOREIGN PATENT DOCUMENTS

| | | |
|---|---|---|
| JP | 2004-181456 | 7/2004 |
| JP | 2008-012095 | 1/2008 |
| JP | 2010-284394 | 12/2010 |
| WO | WO 2013/180240 | 12/2013 |
| WO | WO 2014/024984 | 2/2014 |
| WO | WO 2014/081026 | 5/2014 |

* cited by examiner

ANESTHESIA DEVICE AND METHOD OF CONTROLLING HYDROGEN CONCENTRATION IN A HYDROGEN-CONTAINING ANESTHESIA GAS

TECHNICAL FIELD

The present invention relates to an anesthesia device and a method of controlling hydrogen concentration in a hydrogen-containing anesthesia gas.

This application is the U.S. national phase of International Application No. PCT/JP2016/051399 filed Jan. 19, 2016 which designated the U.S. and claims priority on the basis of Japanese Patent Application No. 2015-009352 filed in Japan on Jan. 21, 2015, the entire contents of each of which are incorporated herein by reference.

BACKGROUND OF THE INVENTION

Conventionally, halogen-based vaporized anesthetics such as sevoflurane and desflurane are often used as general anesthetics for children or newborn babies. However, possibilities in which the use of these vaporized anesthetics as the general anesthetics for children or newborn babies induces apoptosis of brain cells have been suggested, and the possibilities in which the onset of the subsequent cognitive dysfunction is caused have been pointed out.

Thus, in recent years, various studies have been conducted to reduce the apoptosis of brain cells, and it has been reported that an effect can be obtained by simultaneously applying a hydrogen gas at the same time when an anesthetic is used. For example, Patent Document 1 discloses a hydrogen-containing anesthesia gas in which a general anesthetic and hydrogen are combined as a medicine for human or animals other than humans.

DOCUMENTS OF RELATED ART

Patent Literature
Patent Document 1: International Publication No. 2013/180240

SUMMARY OF THE INVENTION

Problems to be Solved by the Invention

Although there are various types of an anesthesia apparatus, a semi-closed circuit-type in which the flow rate is low is mainly used in recent years. In the case where a hydrogen-containing anesthesia gas is used in the semi-closed circuit-type anesthesia apparatus, it is required to accurately measure the amount of an anesthetic or hydrogen circulating in circulation passages.

However, it has been found by the study of the present applicant that there is a case where the hydrogen concentration in a gas circulating in circulation passages cannot be accurately measured.

A device configured to conduct measurement by separating a target gas component in mixed gas, such as a gas chromatography, could realize direct measurement of the mixed gas composed of a vaporized anesthetic and a hydrogen gas. However, such a device is often expensive, and requires the step of separating components, and therefore there is a problem in which continuous measurement cannot be realized.

The present invention was made in view of the above-circumstances, and aims to provide an anesthesia device that can realize an accurate measurement of a hydrogen concentration in a hydrogen-containing anesthesia gas.

In addition, a method of controlling hydrogen concentration in a hydrogen-containing anesthesia gas that can realize an accurate measurement of a hydrogen concentration in a hydrogen-containing anesthesia gas is aimed to be provided.

Means to Solve the Problems

The present invention includes the following aspects.

(1) An anesthesia device including: an anesthesia gas preparation circuit configured to generate an anesthesia gas by mixing an air or an oxygen mixture air with a vaporized anesthetic; a closed circuit-type or semi-closed circuit-type respiratory circuit including a gas circulation passage configured to circulate a hydrogen-containing anesthesia gas containing a hydrogen gas and the anesthesia gas and an interface provided on the gas circulation passage and configured to supply the hydrogen-containing anesthesia gas and recover an exhaled air; a hydrogen concentration measurement circuit configured to measure a hydrogen concentration in a hydrogen-containing anesthesia gas in the gas circulation passage; a gas supply passage provided over the anesthesia gas preparation circuit and the respiratory circuit and configured to supply the hydrogen-containing anesthesia gas to the respiratory circuit; an analytical gas-collecting passage provided over the respiratory circuit and the hydrogen concentration measurement circuit, wherein the hydrogen concentration measurement circuit includes: an anesthetic removing member having a removability of the vaporized anesthetic from the hydrogen-containing anesthesia gas collected from the analytical gas-collecting passage; and a hydrogen concentration measuring instrument provided on the secondary side of the anesthetic removing member.

(2) The anesthesia device according to (1), further including: a hydrogen-containing gas supply circuit configured to supply a hydrogen-containing gas; and a hydrogen-containing gas supply passage configured to supply the hydrogen-containing gas from the hydrogen-containing gas supply circuit, wherein the hydrogen-containing gas supply passage is connected with the gas supply passage between the anesthesia gas preparation circuit and the respiratory circuit.

(3) The anesthesia device according to (2), further including: a control unit configured to control the supply quantity of the hydrogen-containing gas from the hydrogen-containing gas supply circuit based on the measurement value of the hydrogen concentration measured in the hydrogen concentration measurement circuit.

(4) The anesthesia device according to any one of (1) to (3), wherein the vaporized anesthetic is a halogen-based anesthetic.

(5) The anesthesia device according to any one of (1) to (4), wherein the anesthetic removing member is an activated carbon.

(6) A method of controlling hydrogen concentration in a hydrogen-containing anesthesia gas including: collecting a portion of a hydrogen-containing anesthesia gas containing a hydrogen gas and a vaporized anesthetic in a closed circuit-type or semi-closed circuit-type respiratory circuit, removing the vaporized anesthetic therefrom; and then measuring the hydrogen concentration in the hydrogen-containing anesthesia gas.

(7) An anesthesia apparatus mountable kit configured to be mountable on an anesthesia apparatus to supply a hydrogen-containing anesthesia gas in a gas circulation passage and to control a hydrogen concentration in the hydrogen-containing anesthesia gas, the anesthesia apparatus including: an anesthesia gas preparation circuit configured to generate an anesthesia gas by mixing an air or an oxygen mixture air with a vaporized anesthetic; a closed circuit-type or semi-closed circuit-type respiratory circuit including: the gas circulation passage configured to circulate the anesthesia gas; and an interface provided on the gas circulation passage and configured to supply the anesthesia gas and recover an exhaled air; and a gas supply passage provided over the anesthesia gas preparation circuit and the respiratory circuit, and the anesthesia apparatus mountable kit including: a hydrogen-containing gas supply circuit configured to supply the hydrogen-containing gas; a hydrogen-containing gas supply passage configured to connect the hydrogen-containing gas supply circuit with the gas supply passage; an analytical gas-collecting passage configured to collect a gas circulating in the gas circulation passage; a hydrogen concentration measurement circuit configured to measure the hydrogen concentration in the gas collected; and a control unit configured to control a supply quantity of the hydrogen-containing gas from the hydrogen-containing gas supply circuit based on a measurement value of the hydrogen concentration measured; wherein the hydrogen concentration measurement circuit includes: an anesthetic removing member having a removability of the vaporized anesthetic from the gas collected; and a hydrogen concentration measuring instrument provided on a secondary side of the anesthetic removing member.

(8) A veterinary anesthesia device including: an anesthesia gas preparation circuit configured to generate an anesthesia gas by mixing an air or an oxygen mixture air with a vaporized anesthetic; a case configured to accommodate an experimental animal; a hydrogen concentration measurement circuit configured to measure the hydrogen concentration in a hydrogen-containing anesthesia gas containing a hydrogen gas and the anesthesia gas in the case; a gas supply passage provided over the anesthesia gas preparation circuit and the case and configured to supply the hydrogen-containing anesthesia gas to the case; and an analytical gas-collecting passage provided over the case and the hydrogen concentration measurement circuit, wherein the hydrogen concentration measurement circuit includes an anesthetic removing member having a removability of the vaporized anesthetic in the hydrogen-containing anesthesia gas collected from the analytical gas-collecting passage, and a hydrogen concentration measuring instrument provided on the secondary side of the anesthetic removing member.

Effects of the Invention

Since the anesthesia device according to the present invention has a configuration in which a hydrogen concentration measurement circuit configured to measure the hydrogen concentration in a hydrogen-containing anesthesia gas in the gas circulation passage includes: an anesthetic removing member having a removability of a vaporized anesthetic in the hydrogen-containing anesthesia gas and a hydrogen concentration measuring instrument provided on the secondary side of the anesthetic removing member, such that the hydrogen concentration in the hydrogen-containing anesthesia gas is measured by the hydrogen concentration measuring instrument after the vaporized anesthetic in the hydrogen-containing anesthesia gas is removed by the anesthetic removing member, the hydrogen concentration in the hydrogen-containing anesthesia gas can be accurately measured.

According to the method of controlling hydrogen concentration in a hydrogen-containing anesthesia gas of the present invention, since a portion of a hydrogen-containing anesthesia gas containing a hydrogen gas and a vaporized anesthetic in a closed circuit-type or semi-closed circuit-type respiratory circuit is collected, the vaporized anesthetic is removed therefrom, and then the hydrogen concentration in a hydrogen-containing anesthesia gas is measured, it is possible to accurately measure the hydrogen concentration in a hydrogen-containing anesthesia gas from which the vaporized anesthetic is removed.

EMBODIMENTS FOR CARRYING OUT THE INVENTION

Hereinafter, an aspect of an anesthesia device according to the present invention, a method of controlling a hydrogen concentration in a hydrogen-containing anesthesia gas by using the same, an anesthesia apparatus mountable kit, and a veterinary anesthesia device will be explained in detail with reference to the drawings. Note that the drawings cited in the following description may have characterizing portions enlarged to show characteristics clearly, for convenience, and the dimensional proportions of each component may not be the same as the real dimensional proportions.

<Anesthesia Device>

Figure 1:
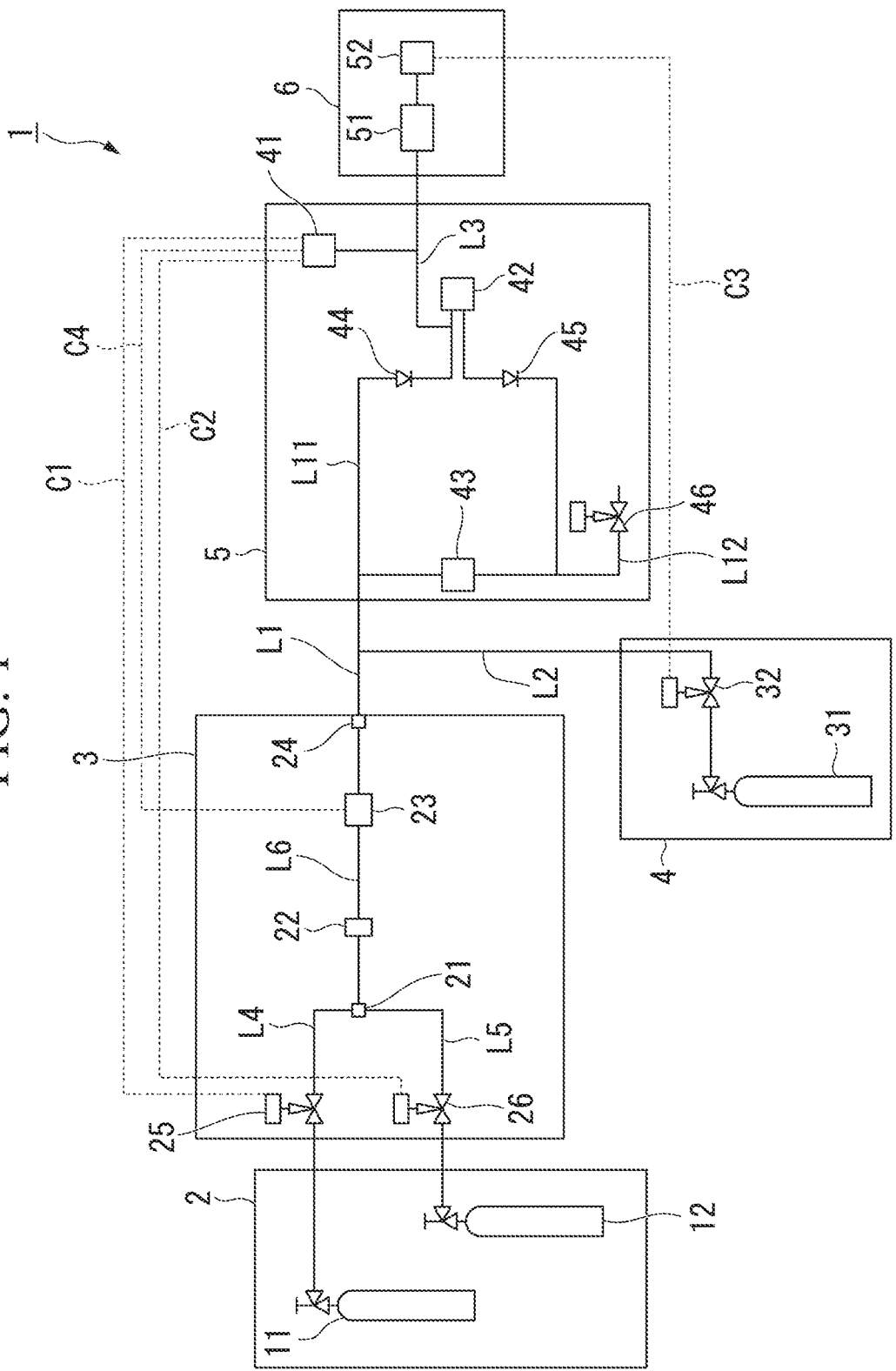
FIG. 1 is a system diagram showing an aspect of an anesthesia device according to the present invention.

FIG. 1 is a system diagram showing a configuration of an aspect of an anesthesia device 1 according to the present invention. The anesthesia device 1 of the aspect includes an anesthesia apparatus and a hydrogen concentration control unit. Specifically, the anesthesia device 1 of the aspect include: a gas supply circuit 2; an anesthesia gas preparation circuit 3; a hydrogen-containing gas supply circuit 4; a respiratory circuit 5; a hydrogen concentration measurement circuit 6; a first gas supply passage L1 (gas supply passage); a hydrogen-containing gas supply passage L2; an analytical gas-collecting passage L3; a second gas supply passage L4; and a third gas supply passage L5, as shown in FIG. 1.

The anesthesia device 1 of the aspect is a device configured to supply to patients a hydrogen-containing anesthesia gas having a hydrogen concentration controlled to a predetermined level by measuring the hydrogen concentration in the hydrogen-containing anesthesia gas circulating in the respiratory circuit 5 by the hydrogen concentration measurement circuit 6, followed by controlling the supply quantity of the hydrogen-containing gas supplied from the hydrogen-containing gas supply circuit 4 based on the measurement value of the hydrogen concentration.

(Gas Supply Circuit)

The gas supply circuit 2 is a circuit configured to supply an oxygen gas and an air to the anesthesia gas preparation circuit 3 and to include an oxygen supply source 11 and an air supply source 12.

The oxygen supply source 11 is an oxygen supply source configured to supply an oxygen gas to an anesthesia gas preparation circuit 3, and is connected with a gas mixer 21 mentioned below via the second gas supply passage L4.

Although the oxygen supply source 11 is not particularly limited, provided that the oxygen supply source 11 is configured to realize supply of an oxygen gas, specific examples thereof include a high pressure oxygen cylinder and a liquid oxygen- or oxygen gas-generator. Although the oxygen gas generator is not particularly limited, provided that the oxygen gas generator is configured to generate an oxygen gas, specific examples thereof include a PSA type oxygen gas generator, and a membrane type oxygen gas generator.

The air supply source 12 is an air supply source configured to supply an air to the anesthesia gas preparation circuit 3, and is connected with a gas mixer 21 mentioned below via the third gas supply passage L5.

Although the air supply source 12 is not particularly limited, provided that the air supply source 12 is configured to realize supply of an air, specific examples thereof include a high pressure air cylinder, a mixed gas composed of an oxygen gas and a nitrogen gas, and an air pressurized by a compressor or the like.

(Anesthesia Gas Preparation Circuit)

The anesthesia gas preparation circuit 3 is a circuit configured to prepare an anesthesia gas from an oxygen gas and an air supplied from the gas supply circuit 2 and a vaporized anesthetic generated by vaporizing an anesthetic in the anesthesia gas preparation circuit 3, and then to supply the prepared anesthesia gas to the respiratory circuit 5. The anesthesia gas preparation circuit 3 includes: a gas mixer 21; a flow meter 22; a vaporizer 23; a gas common outlet 24; an oxygen flow controller 25; an air flow controller 26; and a fourth gas supply passage L6.

The gas mixer 21 is configured to prepare an oxygen mixture air by mixing an oxygen gas and an air supplied from the gas supply circuit 2 and then to supply the oxygen mixture air to the flow meter 22. The term "oxygen mixture air" in the present specification refers to a gas in which an oxygen gas and an air are mixed and the oxygen concentration is higher than that of the air.

Although there is no particular limitation on the gas mixer 21, provided that the gas mixer 21 is configured to realize mixing of the oxygen gas and the air, specific examples thereof include a plate-type mixer, an aspirator-type mixer, a static mixer, a mixing tank, and a T-type fitting.

The flow meter 22 is provided on the fourth gas supply passage L6 to adjust the flow rate of the oxygen mixture air supplied from the gas mixer 21. Although there is no particular limitation on the flow meter 22, specific examples thereof include a float-type flow meter, a flow meter using a platinum catalyst, a Coriolis flow meter, and an ultrasonic flow meter.

Although the vaporizer 23 is not particularly limited, provide that the vaporizer 23 is configured to realize vaporizing of a volatile anesthetic used to prepare an anesthesia gas, specific examples thereof include a thermostatic-type vaporizer and a heating-type vaporizer. The term "anesthesia gas" in the present specification refers to a gas in which the vaporized anesthetic is contained in the air or the oxygen mixture air.

In the anesthesia device 1 of the aspect, any of halogen-based anesthetics such as halothane, methoxyflurane, isoflurane, desflurane, or sevoflurane, and non-halogen-based anesthetics such as diethyl ether may be utilized as the vaporized anesthetic.

There is a problem in which the halogen-based anesthetic has a higher possibility of adversely affecting on the hydrogen concentration measuring instrument 52 in comparison with the non-halogen-based anesthetic. Thus, the anesthesia device 1 of the aspect makes it possible to prevent the adverse effects on the hydrogen concentration measuring instrument 52 due to the halogen-based anesthetic by providing an anesthetic removing member 51 mentioned below. The term "vaporized anesthetic" in the present specification refers to an anesthetic vaporized using a vaporizer or the like.

The gas common outlet 24 is a connection that connects the first gas supply passage L1 with the fourth gas supply passage L6, and is configured to make the anesthesia gas prepared in the anesthesia gas preparation circuit 3 flow out to supply the anesthesia gas to the first gas supply passage L1.

The oxygen flow controller 25 is provided on the second gas supply passage L4 and is configured to adjust the flow rate of the oxygen gas supplied from the oxygen supply source 11.

Although there is no particular limitation on the oxygen flow controller 25, specific examples thereof include valves such as stepless variable valves such as a proportional control valve.

The air flow controller 26 is provided on the third gas supply passage L5 to adjust flow rate of the air supplied from the air supply source 12.

Although the air flow controller 26 is not particularly limited, specific examples thereof include valves such as stepless variable valves such as a proportional control valve.

The first gas supply passage L1 is a pipe provided between the gas common outlet 24 in the anesthesia gas preparation circuit 3 and the gas circulation passage L11 in the respiratory circuit 5. The hydrogen-containing anesthesia gas is prepared in the first gas supply passage L1 by mixing the anesthesia gas supplied from the fourth gas supply passage L6 with the hydrogen-containing gas supplied from the hydrogen-containing gas supply passage L2, and the hydrogen-containing anesthesia gas is supplied to the gas circulation passage L11. The second gas supply passage L4 is a pipe provided between the oxygen supply source 11 and the gas mixer 21. The third gas supply passage L5 is a pipe provided between the air supply source 12 and the gas mixer 21. The fourth gas supply passage L6 is a pipe provided between the gas mixer 21 and the gas common outlet 24. The material of the pipe configuring the respective passages is not particularly limited, and a metal material such as stainless steel or a resin material such as polyester, polypropylene, polyethylene, or vinyl chloride may be used.

(Hydrogen-Containing Gas Supply Circuit)

The hydrogen-containing gas supply circuit 4 is a circuit configured to supply the hydrogen-containing gas to the first gas supply passage L1. The hydrogen-containing gas supply circuit 4 includes a hydrogen supply source 31 and a hydrogen flow controller 32.

The hydrogen supply source 31 is a hydrogen-containing gas supply source configured to supply the hydrogen-containing gas to the first gas supply passage L1, and is connected with the gas common outlet 24 in the anesthesia gas preparation circuit 3 and the gas circulation passage L11 in the respiratory circuit 5 via the hydrogen-containing gas supply passage L2 and the first gas supply passage L1.

Although the hydrogen supply source 31 is not particularly limited, provided that the hydrogen supply source 31 is configured to realize supply of the hydrogen-containing gas, specific examples thereof include a high pressure hydrogen cylinder and a hydrogen gas generator. There is no need that the purity of the hydrogen gas in the high pressure hydrogen cylinder is 100%, and the hydrogen mixed gas in which the hydrogen gas is diluted with an inert gas to below the lower explosive limit for safety may be used. It is preferable that the hydrogen mixed gas diluted with an inert gas to below the lower explosive limit be used in terms of safety. Although there is no limitation on the hydrogen gas generator, provided that the hydrogen gas generator is configured to realize generation of the hydrogen gas, specific examples thereof include a water electrolysis-type hydrogen gas generator and a gas reforming hydrogen gas generator. The term "hydrogen-containing gas" in the present specification refers to a gas containing hydrogen, and encompasses not only the hydrogen gas having a purity of 100% but also a gas diluted with an inert gas.

The hydrogen flow controller 32 is provided on the hydrogen-containing gas supply passage L2 and configured to realize adjusting the flow rate of the hydrogen-containing gas. Although the hydrogen flow controller 32 is not particularly limited, specific examples thereof include valves such as stepless variable valves such as a proportional control valve.

The hydrogen-containing gas supply passage L2 is a pipe provided between the hydrogen-containing gas supply circuit 4 and the first gas supply passage L1 to supply the hydrogen-containing gas to the first gas supply passage L1. Specifically, at one end of the hydrogen-containing gas supply passage L2 is connected with the hydrogen supply source 31, and the other end thereof is connected with the first gas supply passage L1. Thus, the hydrogen-containing gas is supplied to the anesthesia gas between the anesthesia gas preparation circuit 3 and the respiratory circuit 5 to prepare the hydrogen-containing anesthesia gas.

A device configured to prepare a hydrogen-containing anesthesia gas by directing a mixed gas in which an oxygen or an air is mixed with a hydrogen gas in advance into the anesthesia gas preparation circuit 3 and then mixing a vaporizing anesthesia gas with the mixed gas may be proposed. However, there is a problem in which deterioration of a sensor (not shown in the drawings) in the anesthesia gas preparation circuit 3 or an adverse effect on electronic equipment (not shown in the drawing) may be caused by directing the hydrogen-containing gas into the anesthesia gas preparation circuit 3.

In contrast, the above-mentioned configuration of the anesthesia device 1 of the aspect makes it possible to supply the hydrogen-containing anesthesia gas to the respiratory circuit 5 without directing the hydrogen-containing gas into the anesthesia gas preparation circuit 3. Thus, it is possible to prevent the deterioration of a sensor in the anesthesia gas preparation circuit 3 or adverse effect on electronic equipment.

(Respiratory Circuit)

The respiratory circuit 5 is a circuit configured to circulate the hydrogen-containing anesthesia gas supplied from the first gas supply passage L1 in the gas circulation passage L11 in the respiratory circuit 5, to supply the hydrogen-containing anesthesia gas to patients via a mask 42 provided on the gas circulation passage L11 and to recover an exhaled air from the patients.

The respiratory circuit 5 includes: an anesthetic concentration measuring instrument 41; a mask 42 as an interface; a carbon dioxide absorber 43; an intake valve 44; an exhalation valve 45; a surplus gas ejector 46; a gas circulation passage L11; and a gas discharge passage L12. The respiratory circuit 5 employs the semi-closed circuit-type, and the surplus gas ejector 46 makes it possible to eliminate the excess hydrogen-containing anesthesia gas to the outside. The term "hydrogen-containing anesthesia gas" in the present specification refers to an anesthesia gas containing a hydrogen gas, and more specifically a mixed gas composed of a hydrogen gas, a vaporized anesthetic, and an air or an oxygen mixture air.

The anesthetic concentration measuring instrument 41 is provided on the analytical gas-collecting passage L3 and is configured to realize measurement of the concentration of the vaporized anesthetic in the hydrogen-containing anesthesia gas in the gas circulation passage L11. The anesthetic concentration measuring instrument 41 is not particularly limited, provided that the anesthetic concentration measuring instrument 41 is a sensor configured to realize measurement of the concentration of the vaporized anesthetic. Specific examples of the measurement method include a method in which a single wavelength infrared is utilized, a method in which a multi-wavelength infrared is utilized, a method in which piezoelectric elements are utilized, and a method in which photoacoustic is utilized. In addition, the oxygen concentration may be measured by the anesthetic concentration measuring instrument 41.

The anesthetic concentration measuring instrument 41 include a control unit (not shown in the drawings), and is connected with the oxygen flow controller 25 via a signal line C1, with the air flow controller 26 via a signal line C2, and with a vaporizer 23 via a signal line C4.

The mask 42 is provided on the gas circulation passage L11, and configured to supply the hydrogen-containing anesthesia gas. Although the mask 42 is not particularly limited, provided that the mask 42 serves as an interface which realizes supply of the hydrogen-containing anesthesia gas, specific examples thereof include masks such as a respiratory vented mask and full face mask. The mask 42 as an interface may be a mask for administration for humans or animals.

The carbon dioxide absorber 43 is provided on the gas circulation passage L11, and is configured to realize absorption of carbon dioxide contained in the hydrogen-containing anesthesia gas. The carbon dioxide absorber 43 is filled with a carbon dioxide absorbent. Although the carbon dioxide absorbent is not particularly limited, provided that the carbon dioxide absorbent can absorb carbon dioxide, and specific examples thereof include absorbents mainly containing calcium hydroxide and absorbents mainly containing an alkaline solution, a solid carbon dioxide absorbent is preferably used in view of a probability in which the hydrogen-containing anesthesia gas is contaminated when a carbon dioxide absorbent vaporizes.

The intake valve 44 is provided on the primary side of the mask 42 in the gas circulation passage L11, and is configured to prevent the backward flow of the hydrogen-containing anesthesia gas flowing in the gas circulation passage L11. Although the intake valve 44 is not particularly limited, specific examples thereof include a lift-type check valve.

The exhalation valve 45 is provided on the secondary side of the mask 42 in the gas circulation passage L11, and is configured to prevent the backward flow of the hydrogen-containing anesthesia gas flowing in the gas circulation passage L11. Although the exhalation valve 45 is not particularly limited, specific examples thereof include a lift-type check valve.

The surplus gas ejector 46 is provided on the gas discharge passage L12, and is configured to realize emission of an excess hydrogen-containing anesthesia gas. Although the surplus gas ejector 46 is not particularly limited, specific examples thereof include valves such as a back pressure valve.

The gas circulation passage L11 is connected with the first gas supply passage L1, and is an annular pipe configured to circulate the hydrogen-containing anesthesia gas supplied from the first gas supply passage L1. The gas discharge passage L12 is a pipe configured to make the gas circulation passage L11 branch off. Although a material constituting the gas circulation passage L11 and the gas discharge passage L12 is not particularly limited, it is preferable to use a flexible material that permits following of the patient's movement, and specific examples thereof include resin materials such as polyester, polypropylene, polyethylene, and vinyl chloride.

(Hydrogen Concentration Measurement Circuit)

The hydrogen concentration measurement circuit 6 is a circuit configured to collect a portion of the hydrogen-containing anesthesia gas circulating in the respiratory circuit 5 and then measure the hydrogen concentration in a hydrogen-containing anesthesia gas. The hydrogen concentration measurement circuit 6 includes an anesthetic removing member 51 and a hydrogen concentration measuring instrument 52.

The anesthetic removing member 51 is provided on the analytical gas-collecting passage L3 to remove the vaporized anesthetic contained in the hydrogen-containing anesthesia gas. Examples of the anesthetic removing member 51 include solid adsorbents such as an activated carbon and zeolite, organic solvents such as alcohols and ethers, and separation membranes such as a hollow fiber membrane. Among these, a solid absorbent is preferable in terms of handling, and an activated carbon is particularly preferable in terms of the excellent removal performance thereof.

The hydrogen concentration measuring instrument 52 is provided on the secondary side of the anesthetic removing member 51, and realizes measurement of the hydrogen concentration in a hydrogen-containing anesthesia gas from which the vaporized anesthetic is removed by the anesthetic removing member 51. Examples of the hydrogen concentration measuring instrument 52 include a contact burning-type hydrogen analyzer and a specific heat-type hydrogen analyzer. There is a possibility in which the vaporized anesthetic (particularly, the halogen-based vaporized anesthetic) in the hydrogen-containing anesthesia gas effects on a sensor when the anesthesia gas, specifically the hydrogen-containing anesthesia gas containing a halogen-based anesthesia gas is made to pass through the hydrogen analyzer, particularly a contact burning-type hydrogen analyzer. According to the present invention, the anesthetic removing member 51 removes the anesthesia gas in advance, and thereby realizing accurate measurement of the hydrogen concentration by the hydrogen concentration measuring instrument 52.

The hydrogen concentration measuring instrument 52 includes a control unit (not shown in the drawing), and is connected with the hydrogen flow controller 32 via the signal line C3. The supply quantity of the hydrogen-containing gas is adjusted by controlling the hydrogen flow controller 32 based on the hydrogen concentration measured by the hydrogen concentration measuring instrument 52.

The analytical gas-collecting passage L3 has one end connecting with the gas circulation passage L11 and the other end made to be divided in two parts, one of which is connected with the anesthetic concentration measuring instrument 41 and the other of which is connected with the anesthetic removing member 51. It is preferable that the analytical gas-collecting passage L3 be connected with the gas circulation passage L11 at the primary side of the mask 42 and just in front of the mask 42 from the view point of accurate measurement of components in the hydrogen-containing anesthesia gas to be supplied to the mask 42.

<Method of Controlling Hydrogen Concentration in a Hydrogen-Containing Anesthesia Gas>

Next, the method of controlling hydrogen concentration in a hydrogen-containing anesthesia gas utilizing the above-mentioned anesthesia device 1 of the present aspect (hereinafter, simply abbreviated as "method of controlling hydrogen concentration") will be explained.

The method of controlling hydrogen concentrations is a method including: collecting a portion of the hydrogen-containing anesthesia gas containing a hydrogen gas and a vaporized anesthetic in the closed circuit-type or semi-closed circuit-type respiratory circuit; removing the vaporized anesthetic therefrom; and then measuring the hydrogen concentration in the hydrogen-containing anesthesia gas.

The method of controlling hydrogen concentration of the aspect may further include: vaporizing an anesthetic to generate a vaporized anesthetic; mixing the vaporized anesthetic and an oxygen mixture air to obtain an anesthesia gas; mixing the anesthesia gas and a hydrogen-containing gas to prepare a hydrogen-containing anesthesia gas; and then supplying the hydrogen-containing anesthesia gas to the respiratory circuit. The method of controlling hydrogen concentration of the aspect may further include: measuring the hydrogen concentration in a hydrogen-containing anesthesia gas; and then controlling the supply quantity of the hydrogen-containing gas based on the measurement value of the hydrogen concentration to adjust the hydrogen concentration.

Specifically, an oxygen gas supplied from the oxygen supply source 11 and an air supplied from the air supply source 12 are mixed by the gas mixer 21 to prepare an oxygen mixture air. Then, the prepared oxygen mixture air is supplied to the fourth gas supply passage L6. Then, a vaporized anesthetic and the oxygen mixture air supplied from the gas mixer 21 are mixed by the vaporizer 23 to prepare an anesthesia gas. The prepared anesthesia gas is supplied to the first gas supply passage L1 via the gas common outlet 24.

Then, a hydrogen-containing gas supplied from the hydrogen supply source 31 via the hydrogen-containing gas supply passage L2 and the anesthesia gas supplied to the first gas supply passage L1 are mixed in the first gas supply passage L1 to prepare a hydrogen-containing anesthesia gas. Then, the prepared hydrogen-containing anesthesia gas is supplied to the gas circulation passage L11.

The hydrogen-containing anesthesia gas supplied from the first gas supply passage L1 circulates in the gas circulation passage L11. Then, the hydrogen-containing anesthesia gas in the gas circulation passage L11 is supplied to patients via the mask 42 provided on the gas circulation passage L11 during the circulation, and a portion thereof is recovered as an exhaled air. At the time, the exhaled air is recovered in the gas circulation passage L11 in a state in which carbon dioxide is contained therein, and therefore, the carbon dioxide is removed by adsorption with a carbon dioxide absorber 43.

There is a need of adjusting the hydrogen concentration in a hydrogen-containing anesthesia gas circulating in the gas circulation passage L11, since the hydrogen gas in the hydrogen-containing anesthesia gas is partially adsorbed when supplied to patients.

Therefore, the hydrogen concentration in a hydrogen-containing anesthesia gas is measured at the beginning of the method of controlling hydrogen concentration of the aspect. Specifically, the hydrogen-containing anesthesia gas circulating in the gas circulation passage L11 is partially collected as an analytical gas, and then supplied via the analytical gas-collecting passage L3 to the anesthetic removing member 51. Then, the vaporized anesthetic in the hydrogen-containing anesthesia gas is removed therefrom with the anesthetic removing member 51, and then the resultant is supplied to the hydrogen concentration measuring instrument 52. Thus, the hydrogen concentration in the hydrogen-containing anesthesia gas can be measured in the hydrogen concentration measuring instrument 52.

Then, the quantity of the hydrogen-containing gas to be supplied to the first gas supply passage L1 is adjusted based on the measurement value obtained by the measurement of the hydrogen concentration to control the hydrogen concentration in a hydrogen-containing anesthesia gas in the gas circulation passage L11 according to the method of controlling hydrogen concentration of the aspect.

Specifically, the hydrogen concentration measuring instrument 52 sends an opening or closing signal via a signal line C3 to a hydrogen flow controller 32 based on the measurement value of the hydrogen concentration in a hydrogen-containing anesthesia gas to adjust the supply quantity of the hydrogen-containing gas. Specifically, for example, the supply quantity of the hydrogen-containing gas is decreased when the hydrogen concentration in the hydrogen-containing anesthesia gas is high, and is increased when the hydrogen concentration is low. Thus, the hydrogen concentration in a hydrogen-containing anesthesia gas in the gas circulation passage L11 can be adjusted to the required value by adjusting the supply quantity of the hydrogen-containing gas to the first gas supply passage L1.

On the other hand, the vaporized anesthetic contained in the hydrogen-containing anesthesia gas circulating in the gas circulation passage L11 is partially adsorbed when supplied to patients, and therefore the adjustment of the vaporized anesthetic concentration in the hydrogen-containing anesthesia gas is required. Therefore, the vaporized anesthetic concentration in the hydrogen-containing anesthesia gas is measured in the anesthetic concentration measuring instrument 41, and the concentration of the vaporized anesthetic may be controlled by approximately regulating the oxygen flow controller 25, the air flow controller 26, and the vaporizer 23, based on the measurement value thereof.

In the case where the internal pressure of the gas circulation passage L11 increases to more than a certain level due to the oversupply of the hydrogen-containing anesthesia gas, the internal pressure can be decreased by emitting the excess hydrogen-containing anesthesia gas to the outside from the gas discharge passage L12 by the surplus gas ejector 46.

<Anesthesia Apparatus Mountable Kit>

Next, an anesthesia apparatus mountable kit of the other aspect according to the present invention will be explained.

The anesthesia apparatus mountable kit of the aspect is an accessory unit (post-installation unit) configured to be mounted on an anesthesia apparatus to supply a hydrogen-containing anesthesia gas to a gas circulation passage and to control the hydrogen concentration in a hydrogen-containing anesthesia. The "anesthesia apparatus" refers to a general anesthesia apparatus including: an anesthesia gas preparation circuit; a closed circuit-type or semi-closed circuit-type respiratory circuit; and a gas supply passage.

Specifically, the anesthesia apparatus mountable kit of the aspect includes: a hydrogen-containing gas supply circuit configured to supply a hydrogen-containing gas; a hydrogen-containing gas supply passage configured to connect the hydrogen-containing gas supply circuit with a gas supply passage; an analytical gas-collecting passage configured to collect a gas circulating in the gas circulation passage; a hydrogen concentration measurement circuit configured to measure the hydrogen concentration in the collected gas; and a control unit configured to control the supply quantity of the hydrogen-containing gas from the hydrogen-containing gas supply circuit based on the measurement value of the hydrogen concentration. In addition, the hydrogen concentration measurement circuit includes: an anesthetic removing member having a removability of a vaporized anesthetic from the collected gas; and a hydrogen concentration measuring instrument.

The anesthesia apparatus mountable kit of the aspect exhibits the same effects as those of the anesthesia device 1 shown in FIG. 1 by mounting the anesthesia apparatus mountable kit on a conventional anesthesia apparatus.

<Veterinary Anesthesia Device>

Figure 2:
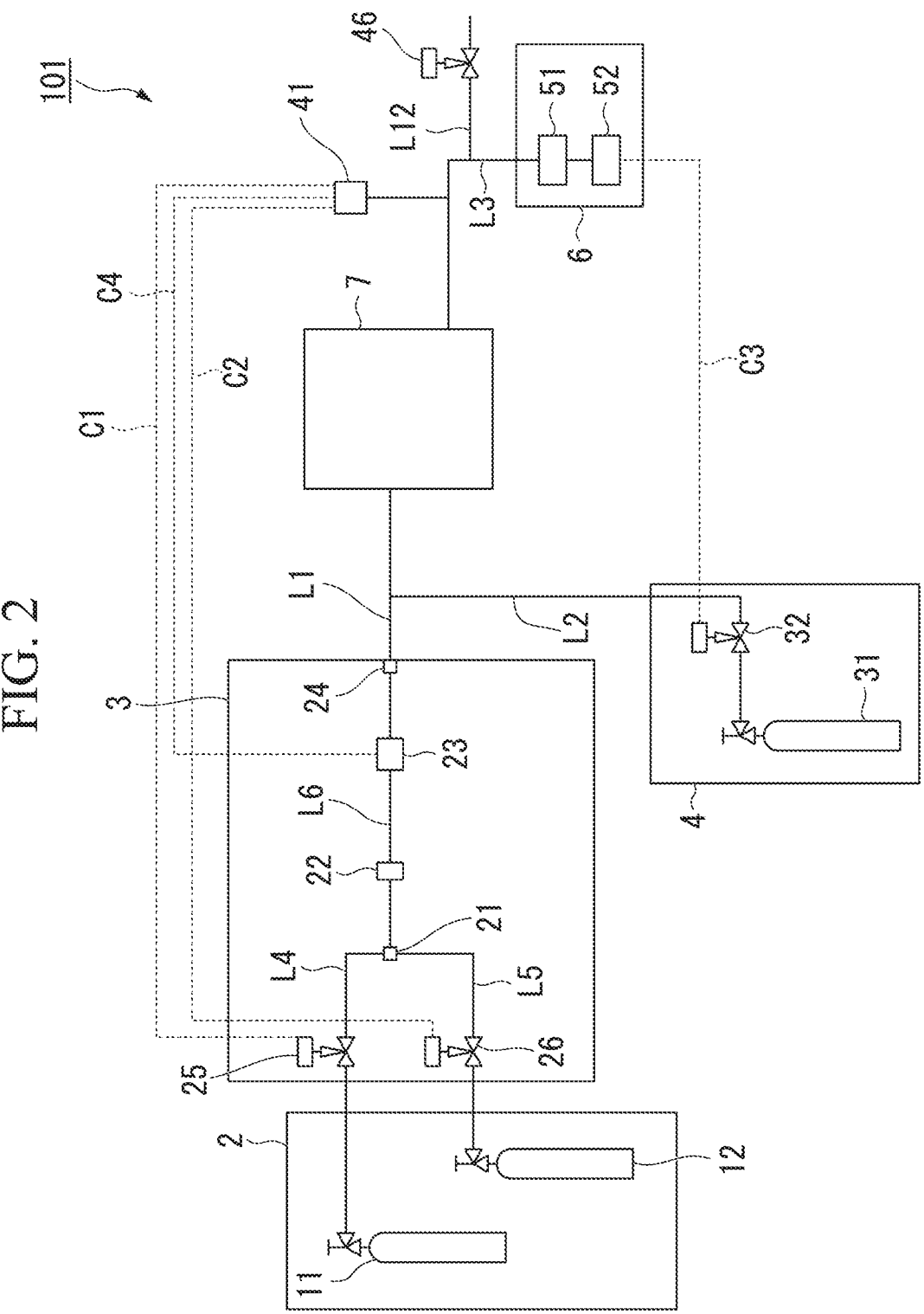
FIG. 2 is a system diagram showing an aspect of a veterinary anesthesia device according to the present invention.

A veterinary anesthesia device 101 of an additional aspect according to the present invention is shown in FIG. 2.

The veterinary anesthesia device 101 has the same configuration as that of the anesthesia device 1 of the first aspect, except that a case 7 configured to accommodate animals is replaced with the respiratory circuit 5 of the human anesthesia device 1 shown in FIG. 1. Accordingly, overlapping elements may be omitted here.

The case 7 may have an arbitrary configuration, provided that the case 7 has a space in which an experimental animal such as mouse, rat, rabbit, dog, or monkey can be accommodated and internal air isolation is realized. The hydrogen-containing anesthesia gas is supplied from a first gas supply passage L1 into the case 7, a portion thereof is directed into a hydrogen concentration measurement circuit 6 via an analytical gas-collecting passage L3, the vaporized anesthetic is removed therefrom with an anesthetic removing member 51, and then the hydrogen concentration is measured by the hydrogen concentration measuring instrument 52. An excess gas supplied to the case 7 to anesthetize the experimental animal is emitted from a gas discharge passage L12 branched from an analytical gas-collecting passage L3. A fan or the like may be provided in the case 7 to make the supplied gas uniform.

The veterinary anesthesia device 101 of the aspect realizes an accurate measurement of the hydrogen concentration in a hydrogen-containing anesthesia gas in the case 7 while suppressing the influence of the anesthesia gas, and thereby making it possible to make the experimental animal inhale the predetermined concentration of the hydrogen gas.

As mentioned above, since the anesthesia device 1 of the aspect realizes measurement of the hydrogen concentration in a hydrogen-containing anesthesia gas by the hydrogen concentration measuring instrument 52 after the vaporized anesthetic in the hydrogen-containing anesthesia gas is removed by the anesthetic removing member 51, an accurate measurement of the hydrogen concentration in a hydrogen-containing anesthesia gas is realized.

In addition, since the anesthesia device 1 of the aspect realizes control of the supply quantity of the hydrogen-containing gas to the first gas supply passage L1 based on the measurement value obtained by measuring the hydrogen concentration in the hydrogen-containing anesthesia gas, the hydrogen concentration in a hydrogen-containing anesthesia gas in the gas circulation passage L11 can be controlled to the required value.

In addition, since the anesthesia device 1 of the aspect has a configuration in which the hydrogen-containing gas supply passage L2 is connected with the first gas supply passage L1 between the anesthesia gas preparation circuit 3 and the respiratory circuit 5, the hydrogen-containing anesthesia gas can be supplied to the respiratory circuit 5 without directing the hydrogen-containing gas into the anesthesia gas preparation circuit 3. As a result, it is possible to prevent the deterioration of sensors in the anesthesia gas preparation circuit 3 or adverse effects on an electronic equipment.

According to the method of controlling hydrogen concentration of the aspect, since a portion of the hydrogen-containing anesthesia gas containing a hydrogen gas and a vaporized anesthetic in the semi-closed circuit-type respiratory circuit 5 is collected, the vaporized anesthetic is removed therefrom, and then the hydrogen concentration in a hydrogen-containing anesthesia gas is measured, the hydrogen concentration in the hydrogen-containing anesthesia gas from which the vaporized anesthetic is removed can be accurately measured.

In addition, according to the method of controlling hydrogen concentration of the aspect, since the supply quantity of the hydrogen-containing gas to the first gas supply passage L1 can be controlled based on the measurement value obtained by measuring the hydrogen concentration in a hydrogen-containing anesthesia gas, the hydrogen concentration in the hydrogen-containing anesthesia gas in the gas circulation passage L11 can be controlled to the required value.

In addition, according to the method of controlling hydrogen concentration of the aspect, since no hydrogen is directed into the anesthesia gas preparation circuit 3 in which an anesthesia gas is prepared, it is possible to prevent the deterioration of equipment in the anesthesia gas preparation circuit 3. In addition, since there is no possibility in which the flow meter 22 is broken, an accurate concentration of the anesthesia gas (thus, an accurate concentration of the hydrogen-containing anesthesia gas) can be stably supplied.

The anesthesia apparatus mountable kit of the aspect makes it possible to exhibit the same effects as those of the above-mentioned anesthesia device 1 by mounting the anesthesia apparatus mountable kit on an anesthesia apparatus having a conventional configuration.

Since the veterinary anesthesia device 101 of the aspect realizes accurate measurement of the hydrogen concentration in a hydrogen-containing anesthesia gas in the case 7 while suppressing the influence of the anesthesia gas, it is possible to make an experimental animal inhale a hydrogen gas at the desired concentration thereof.

Although the aspects of the present invention have been explained in detail with reference to the drawings above, the specific configurations are not limited to the aspects, and a design or the like is also included within a scope not departing from the gist of the present invention. For example, although the anesthesia device 1 shown in FIG. 1 utilizes the semi-closed circuit-type respiratory circuit 5, a closed circuit-type respiratory circuit may be utilized.

In addition, although in the anesthesia device 1 shown in FIG. 1, the gas supply circuit 2 includes the oxygen supply source 11 and the air supply source 12, the air supply source 12 may be used as the oxygen supply source 11, since approximately 21% of oxygen is contained in air.

In addition, although in the anesthesia device 1 shown in FIG. 1, the analytical gas-collecting passage L3 and the gas circulation passage L11 are connected at one place, the analytical gas-collecting passage L3 and the gas circulation passage L11 may be connected at two places composed of the primary side and the secondary side of the mask 42. Thus, it is possible to control the hydrogen concentration in a hydrogen-containing anesthesia gas more accurately.

In the veterinary anesthesia device 101 shown in FIG. 2, the gas discharge passage L12 is branched from the analytical gas-collecting passage L3 connected with the case 7. Although the configuration makes it possible to introduce the gas in the case 7 into the hydrogen concentration measurement circuit 6 uniformly without separately providing a suction pump or the like, the analytical gas-collecting passage L3 and the gas discharge passage L12 may be separately connected with the case 7 depending on the situation.

INDUSTRIAL APPLICABILITY

The anesthesia device and the method of controlling hydrogen concentration in a hydrogen-containing anesthesia gas according to the present invention have applicability in the medical field.

REFERENCE SIGNS LISTS 1 anesthesia device, 2 gas supply circuit, 3 anesthesia gas preparation circuit, 4 hydrogen-containing gas supply circuit, 5 respiratory circuit, 6 hydrogen concentration measurement circuit, 7 case, 11 oxygen supply source, 12 air supply source, 21 gas mixer, 22 flow meter, 23 vaporizer, 24 gas common outlet, 25 oxygen flow controller, 26 air flow controller, 31 hydrogen supply source, 32 hydrogen flow controller, 41 anesthetic concentration measuring instrument, 42 mask (interface), 43 carbon dioxide absorber, 44 intake valve, 45 exhalation valve, 46 surplus gas ejector, 51 anesthetic removing member, 52 hydrogen concentration measuring instrument, 101 veterinary anesthesia device, L1 first gas supply passage (gas supply passage), L2 hydrogen-containing gas supply passage, L3 analytical gas-collecting passage, L4 second gas supply passage, L5 third gas supply passage, L6 fourth gas supply passage, L11 gas circulation passage, L12 gas discharge passage, C1, C2, C3, C4 signal line

The invention claimed is:
1. An anesthesia device comprising:
  an anesthesia gas preparation circuit configured to generate an anesthesia gas by mixing an air or an oxygen mixture air with a vaporized anesthetic;
  a closed circuit-type or semi-closed circuit-type respiratory circuit comprising: a gas circulation passage configured to circulate a hydrogen-containing gas comprising a hydrogen gas and the anesthesia gas; and an interface provided on the gas circulation passage and configured to supply the hydrogen-containing anesthesia gas and recover an exhaled air;
  a hydrogen concentration measurement circuit configured to measure a hydrogen concentration in the hydrogen-containing anesthesia gas in the gas circulation passage the hydrogen concentration measurement circuit comprising: an anesthetic removing member selected from the group consisting of solid adsorbents, organic solvents, and separation membranes; and a hydrogen concentration measuring instrument provided on a secondary side of the anesthetic removing member;
  a gas supply passage provided between the anesthesia gas preparation circuit and the respiratory circuit, and configured to supply the hydrogen-containing anesthesia gas to the respiratory circuit; and
  an analytical gas-collecting passage provided between the respiratory circuit and the hydrogen concentration measurement circuit.
2. The anesthesia device according to claim 1, further comprising:

a hydrogen-containing gas supply circuit configured to supply the hydrogen-containing gas; and a hydrogen-containing gas supply passage configured to supply the hydrogen-containing gas from the hydrogen-containing gas supply circuit, wherein the hydrogen-containing gas supply passage is connected with the gas supply passage between the anesthesia gas preparation circuit and the respiratory circuit.

3. The anesthesia device according to claim 2, further comprising a control unit provided on the hydrogen concentration measuring instrument and configured to control a supply quantity of the hydrogen-containing gas from the hydrogen-containing gas supply circuit based on a measurement value of the hydrogen concentration measured in the hydrogen concentration measurement circuit.

4. The anesthesia device according to claim 1, wherein the vaporized anesthetic is a halogen-based anesthetic.

5. The anesthesia device according to claim 1, wherein the anesthetic removing member is a solid adsorbent.

6. A method of controlling a hydrogen concentration in a hydrogen-containing anesthesia gas, comprising: mixing a hydrogen-containing gas supplied from a hydrogen supply source and an anesthesia gas prepared by a vaporizer to obtain the hydrogen-containing anesthesia gas in a gas supply passage provided between an anesthesia gas preparation circuit and a gas circulation passage provided in a respiratory circuit supplying the hydrogen-containing anesthesia gas to the gas circulation passage; collecting a portion of the hydrogen-containing anesthesia gas from the gas circulation passage; removing the anesthesia gas therefrom; and then measuring the hydrogen concentration remaining in the hydrogen-containing anesthesia gas.

7. An anesthesia apparatus mountable kit configured to be mountable on an anesthesia apparatus to supply a hydrogen-containing anesthesia gas in a gas circulation passage and to control a hydrogen concentration in the hydrogen-containing anesthesia gas, the anesthesia apparatus comprising: an anesthesia gas preparation circuit configured to generate an anesthesia gas by mixing an air or an oxygen mixture air with a vaporized anesthetic; a closed circuit-type or semi-closed circuit-type respiratory circuit comprising: the gas circulation passage configured to circulate the anesthesia gas; and an interface provided on the gas circulation passage and configured to supply the anesthesia gas and recover an exhaled air; and a gas supply passage provided between the anesthesia gas preparation circuit and the respiratory circuit, and the anesthesia apparatus mountable kit comprising:

a hydrogen-containing gas supply circuit configured to supply the hydrogen-containing gas;

a hydrogen-containing gas supply passage configured to connect the hydrogen-containing gas supply circuit with the gas supply passage;

an analytical gas-collecting passage configured to collect a gas circulating in the gas circulation passage;

a hydrogen concentration measurement circuit configured to measure the hydrogen concentration in the gas collected, the hydrogen concentration measurement circuit comprising: an anesthetic removing member selected from the group consisting of solid adsorbents, organic solvents, and separation membranes; and a hydrogen concentration measuring instrument provided on a secondary side of the anesthetic removing member; and a control unit provided on the hydrogen concentration measuring instrument and configured to control a supply quantity of the hydrogen-containing gas from the hydrogen-containing gas supply circuit based on a measurement value of the hydrogen concentration measured.

8. A veterinary anesthesia device comprising:

an anesthesia gas preparation circuit configured to generate an anesthesia gas by mixing an air or an oxygen mixture air with a vaporized anesthetic;

a case configured to accommodate an experimental animal;

a hydrogen concentration measurement circuit configured to measure a hydrogen concentration in a hydrogen-containing anesthesia gas comprising a hydrogen gas and the anesthesia gas in the case, the hydrogen concentration measurement circuit comprising: an anesthetic removing member selected from the group consisting of solid adsorbents, organic solvents, and separation membranes; and a hydrogen concentration measuring instrument provided on a secondary side of the anesthetic removing member;

a gas supply passage provided between the anesthesia gas preparation circuit and the case and configured to supply the hydrogen-containing anesthesia gas to the case; and an analytical gas-collecting passage provided between the case and the hydrogen concentration measurement circuit.

* * * * *